United States Patent [19]

Jansen et al.

[11] 4,430,338

[45] Feb. 7, 1984

[54] METHOD OF TREATMENT PATIENTS AT RISK OF SUDDEN DEATH

[75] Inventors: Frans H. J. Jansen, Gud-Turnhout, Belgium; Peter R. Maroko, Cherry Hill, N.J.

[73] Assignee: Akzo N.V., Netherlands

[21] Appl. No.: 359,133

[22] Filed: Mar. 17, 1982

Related U.S. Application Data

[63] Continuation of Ser. No. 192,625, Sep. 30, 1980, abandoned.

[51] Int. Cl.³ .................. A61K 31/40; A61K 31/495; A61K 27/00
[52] U.S. Cl. ................................ 424/274; 424/250; 424/248.56
[58] Field of Search .................................... 424/274

[56] References Cited
PUBLICATIONS

*J. Pharmacol.* 8, 503, 1977.

*Primary Examiner*—Frederick E. Waddell
*Attorney, Agent, or Firm*—Abelman, Frayne & Rezac

[57] ABSTRACT

The present invention therefore provides a method of treatment patients at risk of so-called sudden death caused by fatal atherothrombosclerotic conditions and which treatment is intended to promote survival, characterized by a chronic administration to the patient of a compound of the general formula

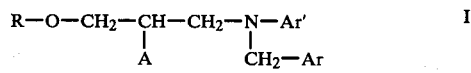

or a pharmaceutically acceptable acid addition salt thereof, in which R represents a straight or branched alkyl group of 1-4 (incl.) carbon atoms, Ar, Ar' represent both an aromatic group, and A is a tertiary amino group selected from di-alkylamino and a nitrogen containing 5- or 6-membered ring, in an effective dialy dosage.

2 Claims, No Drawings

METHOD OF TREATMENT PATIENTS AT RISK OF SUDDEN DEATH

This is a continuation of application Ser. No. 192,625 filed Sept. 30, 1980, now abandoned.

The present invention is dealing with a new therapeutical use of certain 2,3-diamino propanol-1-ethers, which new use brings about a dramatic decrease of mortality in a group of patients at high risk of fatal athero-thrombosclerotic diseases.

Compounds of the general formula I

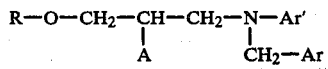

or a pharmaceutically acceptable acid addition salt thereof, in which

R is a straight or branched alkyl group of 1 to 4 (incl.) carbon atoms,

Ar, Ar' represent an aromatic, preferably phenyl, group, and A is a tertiary amino group selected from alkyl (1-6 C) amino and a nitrogen containing 5- or 6-membered ring, are known to possess a distinct cardiovascular activity in that they lower heart rate, especially in case of pronounced tachycardia without interfering with β receptors and without affecting significantly myocardial contractility.

As a consequence of this lower heart rate, the oxygen-consumption is reduced and thus the relative oxygenation of the myocardium is improved. The compounds I were therefore already suggested as medicaments particularly intended for treating Myocardiac anoxemia and angina pectoris.

Some of the compounds I are further known to increase the atrial and atrio-ventricular refractory periods, a property that denotes potential anti-arrhytmic activity (J. Pharmacol. 8, 503, 1977).

Surprisingly it was now found that the compounds of formula I and especially that compound I, in which R is 2-methylpropyl (isobutyl)

Ar and Ar' are phenyl and

A is a pyrrolidino group, positively influence survival of a population at risk of sudden death ("mors subita") caused by fatal atherothrombosclerotic conditions.

This finding is very remarkable because other well known and very effective anti-anginal drugs, anti-hypertensive drugs, platelet aggregation inhibitors and anti-arrhythmic drugs, do not significantly influence survival within a given period of time in a pharmacological test model (that is described more extensively in Example I).

The test results clearly suggest that the occurrence of sudden death at one hand and the occurrence of cardiovascular problems such as anginal conditions, heart-rythm troubles and cardiac deficiencies associated with coronary circulatory problems at the other hand, seem to have no direct relationship at all.

The present invention therefore provides a method of treatment patients at risk of so-called sudden death caused by fatal atherothrombosclerotic conditions and which treatment is intended to promote survival, characterized by a chronic administration to the patient of a compound of the general formula

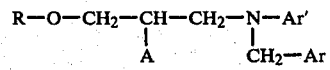

or a pharmaceutically acceptable acid addition salt thereof, in which

R represents a straight or branched alkyl group of 1-4 (incl.) carbon atoms,

Ar, Ar' represent both an aromatic group, and

A is a tertiary amino group selected from di-alkylamino and a nitrogen containing 5- or 6-membered ring, in an effective daily dosage of from 1-50 mg/kg body weight if administered orally or rectally and from 0,5-25 mg/kg body weight, where administered parenterally.

A further embodiment of the present invention provides a composition of matter which prevents or decrease the chance of so-called sudden death in a group of patients at high risk of fatal athero-thrombosclerotic diseases, comprising a compound of formula I defined above in admixture with one or more pharmaceutically acceptable carriers or diluents.

The symbol R in the compounds of formula I may represent i.a. methyl, ethyl, propyl, isopropyl, n.butyl, isobutyl, t.butyl.

The isobutyl group and isopropyl groups are to be preferred.

The aromatic groups Ar and Ar' are preferably phenyl, but may also be other aromatic groups such as pyridine.

The definition of A being a tertiary amino group, encompasses a di-alkyl amino group, in which the alkyl group has 1-6 (incl.) carbon atoms, such as methyl, ethyl and propyl, or represents a nitrogen containing 5- or 6-membered ring, such as piperidino, pyrrolidino and morpholino.

The new method of treatment and composition of matter also include pharmaceutically acceptable acid addition salts of the compounds of formula I, such as the hydrochloric acid, fumaric acid, maleic acid or succinic acid salts.

Most preferred compound to be used in the present invention is the compound of formula I, in which R represents isobutyl, Ar and Ar' are both phenyl and A represents pyrrolidino, and an acid addition salt thereof.

The new method of treatment encompasses a chronic administration of the compounds of formula I which can take place either orally (or rectally) by means of solid dosage unit forms such as pills, tablets, capsules or suppositories, or parenterally by means of a liquid injection preparation or implants. The oral or rectal administration of a compound I takes place in a daily dosage of from 1-50 mg/kg body weight and more preferably in a daily dosage of from 2-10 mg/kg.

The parenteral administration preferably requires a daily dosage of from 0,5-25 mg/kg body weight and more preferably a dosage of from 1-10 mg/kg.

EXAMPLE I

Description of Test Model and Test Results

Inbred Japanese quails (*Coturnix japonica*), when fed a cholesterol enriched diet, develop sudden death caused by fatal atherosclerosis or atherothrombosclerosis. Quails on normal diet generally survive for several years.

Mortality in groups of 50 quails, fed on normal diet for periods of 9 months, was in average 4%. In contrast quails, fed on 2% cholesterol added to their normal diet, die much earlier; an average of 80% were dead within 9 months.

In many quails (suddenly died) the brain was studied to verify whether the cause of death could be a cerebral vascular accident. However, indications for such cerebral damage were not found.

In order to test the influence of various drugs on atherosclerosis and sudden death, quails were divided into two groups viz.

(a) the test group fed on normal diet to which 2% cholesterol and the drug to be tested were added, and (b) the control group fed on 2% cholesterol added to the normal diet.

| drug | dose in mg/kg/ day | death in test group in % | death* in control group in % | period covered in months |
|---|---|---|---|---|
| sulfinpyrazone (Anturan (R)) | 100 | 62 | 58 | 8 |
| propranolol (Inderal (R)) | 30 | 68 | 68 | 8 |
| acetylsalicylic acid (Sigma Chemicals) | 15 | 42 | 42 | 6 |
|  | 10 | 68 | 62 | 8 |
| Quinidine sulphate | 100 | 42 | 42 | 6 |
| Procainamide | 100 | 46 | 42 | 6 |

*Average death in control group fed on normal diet was 4%.

None of the above-mentioned drugs influence survival in a statistically significant manner.

To investigate the effects of a compound of the invention on survival, namely 2 mg/kg/day of β(2-methyl-propoxy)methyl (N-phenyl-N-phenylmethyl)-1-pyrrolidine-ethanamine.HCl-H$_2$O, 42 quails were used, 9 of them served as "environmental controls" (fed on normal diet) and 33 were fed with 2% cholesterol added to the normal diet. These quails were randomized to a control group of 15 quails and a test group of 18 quails. The latter group additionally received the above-mentioned compound of the invention. Within 6 months none of the environmental controls died. All 15 quails of the control group (on cholesterol diet) diet, while only 5 out of 18 quails in the said drug treated test group died. This difference is statistically significant.

EXAMPLE II

Injection Preparation

A sterile composition is prepared consisting of per ml:
active ingredient*)—4 mg
glucose—44 mg
water for injection up to—1 ml

*) β(2-methylpropoxy)methyl(N-phenyl-N-phenylmethyl) 1-pyrrolidine-ethanamine.HCl.H$_2$O.

Ampoules were filled either with 1 ml or with 2 ml of this composition.

EXAMPLE III

Tablets

Lactose is mixed with potato starch and the active compound. The mixture is kneaded with an aqueous solution of povidone. The resulting mass is passed through a Fitzmill, dried, regranulated and then mixed with potato starch and microcrystalline cellulose. Finally the lubricant magnesium stearate is admixed.

The granulate is compressed to tablets, which are then provided with a while film-coat.

Constituents per tablet:
β(2-methylpropoxy)methyl (N—phenyl-N—phenylmethyl) 1-pyrrolidine-ethanamine monohydrochloride monohydrate (formula I: R = isobutyl; Ar/Ar' = phenyl; A = pyrrolidino)   100 mg
potato starch   20 mg
microcrystalline cellulose   10 mg
povidone   6 mg
magnesium stearate   2 mg
lactose   62 mg
                                                    200 mg Tablet coating (per tablet)
hydroxy propyl methyl cellulose   approx.   5 mg
polyethylene glycol 6000   approx.   1 mg
titanium dioxide   approx.   1 mg

We claim:

1. A method of treating patients at risk of sudden death caused by atherosclerosis or atherothrombosclerosis, characterized by the chronic administration to said patients of a compound of the formula I $$R-O-CH_2-CH-CH_2-N-Ar' \quad\quad I$$
$$\phantom{R-O-CH_2-}|\phantom{CH-CH_2-N}|$$
$$\phantom{R-O-CH_2-CH-CH_2-N}A\phantom{-}CH_2-Ar$$

or a pharmaceutically acceptable acid addition salt thereof, in which R represents isobutyl, Ar and Ar' both are phenyl and A is pyrrolidino in an effective daily dosage from 1–50 mg/kg body weight when administered orally or rectally and from 0.5–25 mg/kg when administered parenterally.

2. Method according to claim 1 in which the active compound is:

$$CH_3\!\!\diagdown\!\!CH-CH_2-O-CH_2-CH-CH_2-N-\!\!\langle\text{phenyl}\rangle \cdot HCl\cdot H_2O$$
$$CH_3\diagup \phantom{CH-CH_2-O-CH_2-}\underset{\underset{\text{pyrrolidine}}{|}}{N}\phantom{-CH_2-N}\underset{CH_2-\langle\text{phenyl}\rangle}{|}$$

* * * * *